United States Patent [19]

Hess, III et al.

[11] 4,175,558

[45] Nov. 27, 1979

[54] APPARATUS FOR ADMINISTERING PARENTERAL LIQUID IN SEQUENTIAL UNITS PROVIDED WITH A BALL VALVE FLOAT

[75] Inventors: John M. Hess, III, Carpentersville; Herbert Mittleman, Deerfield, both of Ill.

[73] Assignee: Baxter Travenol Laboratories, Inc., Deerfield, Ill.

[21] Appl. No.: 816,107

[22] Filed: Jul. 15, 1977

[51] Int. Cl.² .............................................. A61M 5/14
[52] U.S. Cl. ................................. 128/214 C; 128/274; 137/242; 137/331; 137/399; 222/67
[58] Field of Search ............ 128/214 R, 214 C, 214.2, 128/227, 213, 274; 222/67; 137/399, 449, 238, 242, 330, 331

[56] References Cited

U.S. PATENT DOCUMENTS

| 954,178 | 4/1910 | Fowler | 137/331 |
|---|---|---|---|
| 1,519,832 | 12/1924 | Griffin | 137/449 X |
| 3,207,372 | 9/1965 | Evans | 128/214 C X |
| 4,055,176 | 10/1977 | Lundquist | 128/214 C |
| 4,078,563 | 3/1973 | Tuseth | 128/214 C |

Primary Examiner—Dalton L. Truluck
Attorney, Agent, or Firm—John P. Kirby, Jr.; Paul C. Flattery; Garrettson Ellis

[57] ABSTRACT

A parenteral liquid administering device includes an enlarged, liquid-holding burette-type chamber for receiving measured aliquots of liquid from a source. The burette has a bottom flow aperture with a valve controlling flow through the aperture. The valve includes a buoyant float ball and a valve seat positioned about the bottom flow aperture to receive the ball, in the absence of sufficient liquid to float it, in air-tight, sealing relation. Apertured retention means are provided surrounding the ball which are proportioned to permit it to float in spaced relation from the valve seat in the presence of liquid passing through the apertured retention means.

9 Claims, 3 Drawing Figures

APPARATUS FOR ADMINISTERING PARENTERAL LIQUID IN SEQUENTIAL UNITS PROVIDED WITH A BALL VALVE FLOAT

BACKGROUND OF THE INVENTION

In Scislowicz U.S. Pat. No. 3,216,418, a burette-type administration set is described having a burette chamber with a bottom flow aperture and a float-type valve controlling flow through the aperture. The purpose of this type of structure is to prevent the further draining of the set when the burette chamber is empty, so that air is not placed into the lower portion of the administration set, with the consequent danger that upon the refilling of the burette chamber the weight of the solution might drive air bubbles through the set into the patient.

Problems, however, have arisen with hinged float and floating disc-type valves, as shown in this patent, in that they occasionally fail to perform the function for which they are intended, with the structures utilized in the patent becoming "hung-up", and failing to properly close. In the absence of a proper closure, upon emptying of the burette chamber, air continues to pass through the bottom aperture of the chamber, which in turn permits the liquid level of the set to drop. When this happens, if noticed, the set must be removed from the patient and reprimed. If not noticed, the patient is in danger of receiving air along with the parenteral solution, which can be life-threatening in serious situations.

Also, a similar device is sold in which the valve at the bottom aperture of the burette set is a porous, hydrophilic membrane. This valve has no moving parts to get out of order, and thus can be extremely reliable. However, some medicaments which would be desirably added to the burette chamber, and are of low solubility, may be undesirably filtered out and clog the filter membrane valve. Also, it has been found that the device requires a small amount of extra training to learn how to use it properly. Untrained people have been found, on occasion, to break the membrane valve during their attempted priming of the set, which of course largely inactivates the membrane valve.

It has been found that the device of this invention, being a floating ball valve, is more easily utilized by inadequately trained personnel, since there is no membrane to break. Accordingly, there is also no problem of clogging of the membrane due to various supplemental medications that desirably might be added to the burette chamber.

Furthermore, the parenteral liquid administering device of this invention has been found to exhibit greater reliability in its valve closure characteristics than flap valves and the like, resulting in fewer failures of the product. This in turn greatly reduces the risk that a patient may be subjected to an air embolism, as well as eliminating the necessity to remove defective sets from use and to replace them with a new set, making a new venopuncture in the patient's arm.

DESCRIPTION OF THE INVENTION

This invention relates to a parenteral liquid administering device which comprises tubular means for administering parenteral liquid to a patient. Means for connecting the device to a source of such liquid, such as a spike on one end of the set, are provided. An enlarged, liquid-holding chamber is positioned in flow communication with the tubular means for administering parenteral liquid, and also positioned to permit filling of the chamber with liquid passing through the connecting means. The chamber includes the bottom flow aperture, and a valve for controlling flow through the aperture.

In accordance with this invention, the valve at the bottom flow aperture of the enlarged liquid chamber includes a bouyant float ball, and a valve seat positioned about the bottom flow aperture to receive the ball, in the absence of sufficient liquid to float it, in air-tight, sealing relation. Apertured retention means are also provided, surrounding the ball to define a generally cylindrical chamber and proportioned to retain the ball therein, to permit it to float in spaced relation from the valve seat in the presence of sufficient liquid.

As an added advantage, an annular step is provided in the retention means around the ball below its center of gravity, in the closed position. This has been found to create liquid turbulence, that washes the ball and valve seat to remove gummy precipitates, and also to help lift the ball from the seat upon reinstitution of flow.

Accordingly, when the enlarged, liquid-holding chamber contains a substantial amount of liquid, the bouyant float ball will float upwardly away from the valve seat. As the liquid drains through the bottom aperture, the ball is brought down onto the valve seat, guided by the apertured retention means, to form an air-tight, generally annular seal between the ball and the valve seat. This seal is enhanced in the typical case when the tubular means for administering the parenteral liquid communicates with the bottom flow aperture, and is positioned in use to extend downwardly therefrom. In this instance, after the ball has seated on the valve seat upon emptying of the liquid-holding chamber, a suction pressure head may be developed as the liquid in the tubular means is urged downwardly by the force of gravity. This suction head quickly prevents the draining of a major amount of the liquid from the tubular means, and at the same time serves to press the float ball more strongly against the valve seat, increasing the quality of the seal.

While float members have been used in parenteral liquid administration sets previously (see for example U.S. Pat. Nos. 3,963,024; 3,035,575; 3,021,841; and 2,907,325) the reliable, inexpensive valving system of this invention for a burette-type administration set is novel, and possesses a combination of advantages not found together in the prior art.

Referring to the drawings.

Figure 1:
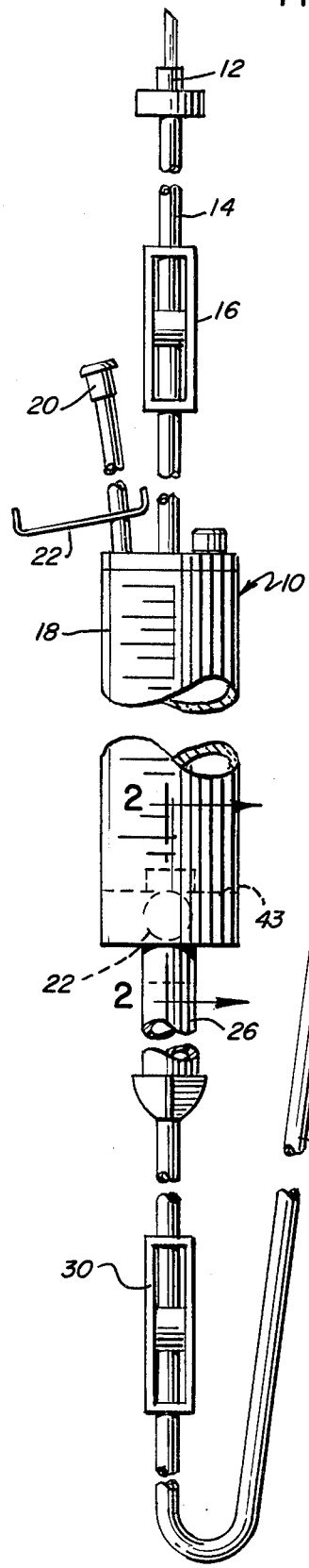
FIG. 1 is an elevational view of a typical parenteral liquid administering set of this invention.

Referring to the drawings, solution administration set 10 is illustrated. The set comprises a conventional pointed connector member 12, positioned at the end of flexible tubing 14 for connection with a source of parenteral liquid such as normal saline solution, physiological glucose solution, blood, or blood plasma, or other blood components.

Clamp 16 controls fluid flow through tubing 14 into an enlarged, liquid-holding burette chamber 18, comprising a plastic tube, sealed at both ends, which may have volumetric graduations inscribed on it to serve as a liquid measuring chamber.

A filter-carrying vent member 20 of conventional construction may also be provided, with a clamp 22 controlling the flow through the vent. This permits the emptying of chamber 18 without opening clamp 16.

At the bottom of chamber 18, a flow aperture 22 is designed to pass through a constricted-bore tubular drop-forming member 23, which, in turn, is carried as part of valve member 24.

Drop-forming member 22 communicates with a drip chamber 26 of conventional construction. Flexible tubing 28 communicates with the bottom of drip chamber 26, and is conventionally equipped with a clamp 30, a Y-injection site 32, a latex flashback device for determining proper venopuncture 34, and a needle adapter 36 for receiving the phlebotomy needle.

Figure 2:
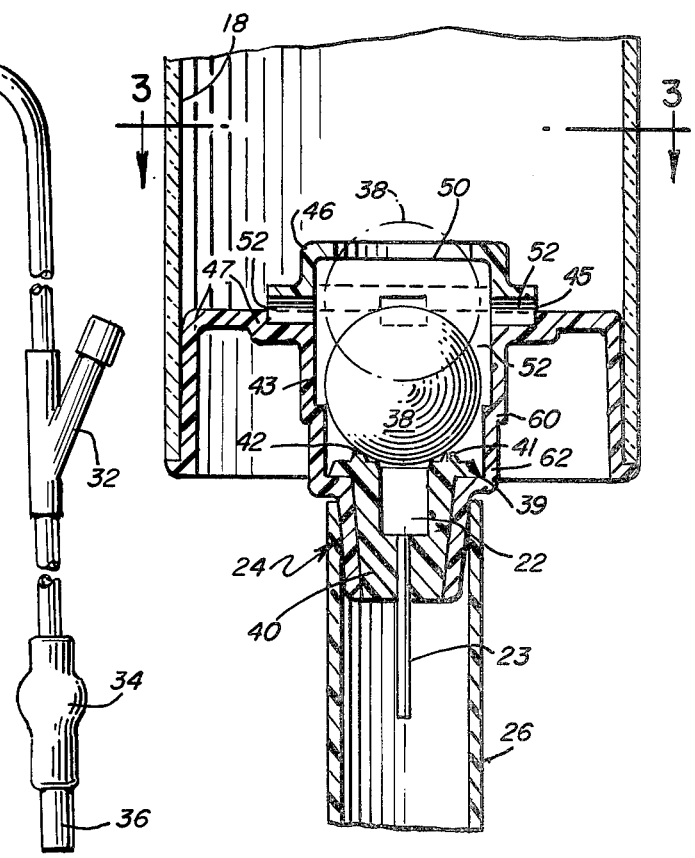
FIG. 2 is a vertical sectional view taken along line 2—2 of FIG. 1, but greatly enlarged, of the portion of the administration set of FIG. 1, showing the floating ball valve of this invention at the bottom of the enlarged, liquid-holding chamber.

In accordance with this invention, the valve controlling liquid access through the bottom aperture 22 includes a bouyant float ball 38 which is positionable to rest as shown in FIG. 2 in solid lines on a valve seat 40. Valve seat 40 is retained by flange 39 in tubular closure member 43. Preferably, the valve seat 40 may also be used to carry the tubular, drop-forming member 23, defining part of bottom flow aperture 22 by frictional fit within a corresponding aperture defined in valve seat 40. Valve seat 40 may preferably be made of a resilient, rubbery material such as natural latex, defining an annular ring 41, to facilitate sealing about an annular seal line of contact 42 between valve seat 40 and ball 38, when ball is resting on the seat 40.

Preferably, when the tubular drip chamber 26 and the flow tubing 28 are positioned below burette chamber 18, to extend downwardly therefrom, a suction pressure head, resulting from the effect of gravity on the liquid in the tubing 28 and drip chamber 26 is provided. This, in turn, is exerted against the seated ball 38 to assist in the airtight sealing of valve 24 by increasing the pressure of ball 38 against valve seat 40.

Figure 3:
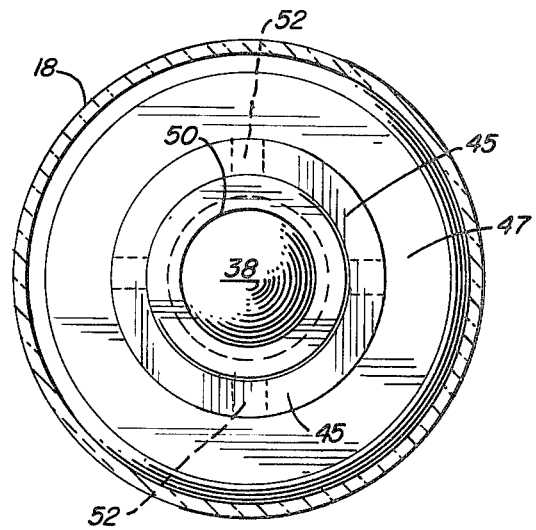
FIG. 3 is a transverse sectional view of the administration set of FIG. 2, taken along line 3—3 of FIG. 2.

Apertured retention means are provided to retain float ball 38, which is preferably of a diameter of less than half the width of burette chamber 18, as shown in FIG. 2. The retention means includes lower tubular member 43, which carries an upper closure member 46 sealed thereto by flange 45, attached to upper surface 47. Closure member 46 defines an upper aperture 50 of a transverse dimension which is smaller than the diameter of float ball 38, for retention thereof. Also, lateral apertures 52 may be defined between members 43, 46, so that liquid can pass through the apertured retention means in all positions of ball 38. In this specific embodiment, four lateral apertures 52, spaced 90 degrees apart, are provided by appropriately shaped cavities in members 43, 46, as shown in FIGS. 2 and 3.

Upper retaining member 46 can be joined to upper surface 47, which is part of lower member 43, by solvent sealing, heat sealing, or the like after ball 38 and valve seat 40 have been inserted into the well 52 defined in member 43. Member 43 also serves as an end closure for burette chamber 18, as shown.

Accordingly, when burette 18 is at least partially filled with solution, float ball 38 floats upwardly from valve seat 40, being limited in its upward motion by upper retention member 46, as shown by ball 38 in phantom lines. As the parenteral liquid is drained from the burette chamber, ball 38 is allowed to descend onto ring 41 of valve seat 40, to define the annular line of contact 42 between valve seat 40 and ball 38. The diameter of the ring 41 and line of contact 42, and the diameter of the tubular portion of diameter 43 is preferably proportioned to prevent ball 38 from moving substantially laterally to such a degree that the center of balance of ball 38 can be positioned outwardly of the circumference of line of contact 42. Thus, ball 38 is urged to spontaneously seat on ring 41 in the normal instances when the burette chamber 18 is positioned generally vertically.

Accordingly, with successive emptyings of liquid aliquots placed in burette chamber 18 from a source of liquid supply, connected to the set by means of connector 12, valve 24 opens and closes by the action of float ball 38, spontaneously and with improved reliability over hinged disc valve members and the like, and without encountering the problems of clogging of a filter membrane valve in the presence of certain additives, and breaking of the valve.

In accordance with this invention, lower member 43 defines an annular inward step 60, so that the lower portion of the chamber which holds ball 38 is slightly constricted with respect to the upper portion. The result of this is to create a turbulent flow rather than an laminar flow of liquid flowing downwardly through aperture 50, for example upon reinstitution of flow into the burette member 18 by the opening of valve 16.

Annular step 60 is preferably positioned below the center of gravity of ball 38 as it rests upon the valve seat, as shown in FIG. 2.

The effect of the turbulent flow created by the annular step is to more effectively urge the ball away from the valve seat when roller member 43 becomes filled with liquid, overcoming any adhesion forces between the ball 38 and valve seat 40 which may exist. Also, the turbulent flow created by step 60 has been found to assist in removing precipitated materials from the valve seat and the ball 38, to avoid the problem of obtaining poor, uneven seating of ball 38 on the valve seat with resulting leakage, as well as avoiding an adhesion problem between the ball and the valve seat.

This is highly advantageous when using parenteral solutions containing, for example, keflin, which readily precipitates out of solution, or dextrose, which can form a gummy film by precipitation. The presence of step 60 in conjunction with the slightly constricted lower portion of the chamber retaining the ball 38 tends to reduce the deposit of such undesirable precipitates on the valve seat.

Also, the turbulence generated by step 60 causes the ball 38 to rotate as it operates, which is also advantageous for avoiding leakage.

The constricted portion 62 of the chamber defined by lower member 43 for retaining ball 38 is preferably not significantly less in diameter than the diameter of ball 38, and spaced therefrom in all positions of the ball. As shown in FIG. 2, its diameter is essentially identical to that of ball 38.

The above has been offered for illustrative purposes only and is not for the purpose of limiting the invention of this application, which is as defined in the claims below.

That which is claimed is:

1. In a parenteral liquid administering device which comprises tubular means for connecting said device to a source of said liquid, and an enlarged, liquid-holding chamber positioned in flow communication with said tubular means, said chamber including a bottom flow aperture, and a valve controlling flow through said aperture, the improvement comprising, in combination:

said valve including: a buoyant float ball, a valve seat positioned about said bottom flow aperture to receive said ball in air-tight sealing relation in the absence of sufficient liquid to float said ball, and apertured retention means surrounding said ball and proportioned to permit it to float in spaced relation from said valve seat in the presence of liquid passing through said apertured retention means, said apertured retention means defining a generally cylindrical chamber, said chamber defining an annular step positioned upstream from said valve seat and extending in generally normal relation to the axis of said enlarged liquid holding chamber, said annular step being positioned about said float ball when positioned on the valve seat whereby turbulent flow of liquid is created upon filling said retention means with the liquid.

2. The parenteral liquid administering device of claim 1 in which said annular step occupies a position below the center of gravity of said float ball when positioned on said valve seat.

3. The device of claim 1 in which the diameter of the lower constricted portion of said chamber defined in the apertured retention means is of a diameter essentially equal to the diameter of said float ball, and spaced therefrom.

4. The device of claim 1 in which said tubular means for administering parenteral liquid communicates with said bottom flow aperture and is positioned in use to extend downwardly therefrom, whereby a suction pressure head can be exerted against said seated ball by liquid in the tubular means to assist in air-tight sealing of the valve.

5. The device of claim 4 in which said ball is of a diameter of no more than half of the width of said enlarged, liquid holding chamber, and said apertured retention means is proportioned to restrict the lateral movement of said float ball to a fraction of the width of said enlarged, liquid holding chamber.

6. The device of claim 5 in which said apertured retention means defines an upper, circular aperture positioned to be occluded by said float ball when submerged in liquid, and said apertured retention means further defines a plurality of lateral apertures positioned whereby they cannot be simultaneously occluded by said float ball in any position.

7. The device of claim 6 in which said valve seat is made of a resilient material to facilitate the formation of an annular sealed line with the float ball in the absence of sufficient parenteral liquid to float said ball.

8. The device of claim 7 in which said apertured retention means defines a lower aperture which receives the valve seat, said valve seat further defining an outwardly extending flange for securance in said lower aperture.

9. The device of claim 8 in which said valve seat carries a downwardly extending tubular drop-forming member.

* * * * *